(12) United States Patent
Henschke et al.

(10) Patent No.: US 8,846,958 B2
(45) Date of Patent: Sep. 30, 2014

(54) PROCESS FOR THE PREPARATION OF LUBIPROSTONE

(75) Inventors: Julian Paul Henschke, Tainan (TW); Yuanlian Liu, Suzhou (CN); Lizhen Xia, Suzhou (CN); Yung-Fa Chen, Tainan (TW)

(73) Assignee: Scinopharm (Kunshan) Biochemical Technology Co., Ltd., Kunshan (CN)

( * ) Notice: Subject to any disclaimer, the term of this patent is extended or adjusted under 35 U.S.C. 154(b) by 0 days.

(21) Appl. No.: 13/876,418

(22) PCT Filed: Nov. 16, 2010

(86) PCT No.: PCT/CN2010/001614
§ 371 (c)(1),
(2), (4) Date: Mar. 27, 2013

(87) PCT Pub. No.: WO2012/048447
PCT Pub. Date: Apr. 19, 2012

(65) Prior Publication Data
US 2013/0225842 A1    Aug. 29, 2013

(51) Int. Cl.
*C07D 311/74* (2006.01)
*C07C 33/42* (2006.01)
*C07C 405/00* (2006.01)
*C07D 311/94* (2006.01)
*C07C 29/143* (2006.01)
*C12P 31/00* (2006.01)

(52) U.S. Cl.
CPC .............. *C07D 311/74* (2013.01); *C07C 33/42* (2013.01); *C12Y 301/01003* (2013.01); *C07C 405/00* (2013.01); *C07D 311/94* (2013.01); *C07C 29/143* (2013.01); *C12P 31/00* (2013.01); *C07C 2101/08* (2013.01)
USPC ............ 549/396; 556/112; 556/441; 568/843

(58) Field of Classification Search
CPC .... C07C 29/143; C07C 33/42; C07C 405/00; C07C 2101/08; C07D 31/94; C07D 311/74; C12Y 301/01003
USPC .................... 549/396; 556/441, 112; 568/843
See application file for complete search history.

(56) References Cited

U.S. PATENT DOCUMENTS

| | | | |
|---|---|---|---|
| 7,355,064 B2 | 4/2008 | Hirata et al. | |
| 2009/0259058 A1* | 10/2009 | Henschke et al. | 549/501 |
| 2012/0309990 A1* | 12/2012 | Weeratunga et al. | 549/396 |

FOREIGN PATENT DOCUMENTS

| | | |
|---|---|---|
| WO | 9501179 A1 | 1/1995 |
| WO | 2006080549 A2 | 8/2006 |
| WO | 2006093348 A2 | 9/2006 |
| WO | 2010083597 A1 | 7/2010 |

OTHER PUBLICATIONS

E. J. Corey, J. Am. Chem. Soc., 1969, 91, pp. 5675-5676.
Elias James Corey, Angew. Chem. Int. Ed. Engl., 1991, 30, pp. 455-465.

* cited by examiner

*Primary Examiner* — Noble Jarrell
*Assistant Examiner* — John Mauro
(74) *Attorney, Agent, or Firm* — Enshan Hong; Kent H. Cheng; VLP Law Group LLP

(57) ABSTRACT

Processes for preparing and purifying lubiprostone are disclosed. Intermediates and preparation thereof are also disclosed.

22 Claims, No Drawings

PROCESS FOR THE PREPARATION OF LUBIPROSTONE

BACKGROUND

1. Field of the Invention

The present invention provides for an efficient synthetic process for making lubiprostone.

Lubiprostone, 7-[(1R,3R,6R,7R)-3-(1,1-difluoropentyl)-3-hydroxy-8-oxo-2-oxabicyclo[4.3.0]non-7-yl]heptanoic acid, is the active pharmaceutical ingredient (API; drug substance) in the drug product Amitiza®, a gastrointestinal agent used for the treatment of Chronic Idiopathic Constipation in adults. It is marketed by Sucampo Pharmaceuticals, Inc. and was approved by the United States Food and Drug Administration (FDA) on Jan. 31, 2006. It is also approved by FDA to treat Irritable Bowel Syndrome with constipation (ISB-C) in adult women aged 18 and over on Apr. 29, 2008. Amitiza® is also being clinically tested for other gastrointestinal disorders. Lubiprostone is a bicyclic 13,14-dihydro-15-keto-16,16-difluoro-prostaglandin E1 derivative (a.k.a., a so-called 13,14-dihydro-15-keto-prostaglandin derivative). Prostaglandins possess the prostanoic acid backbone which is a C20 fatty acid (Figure 1).

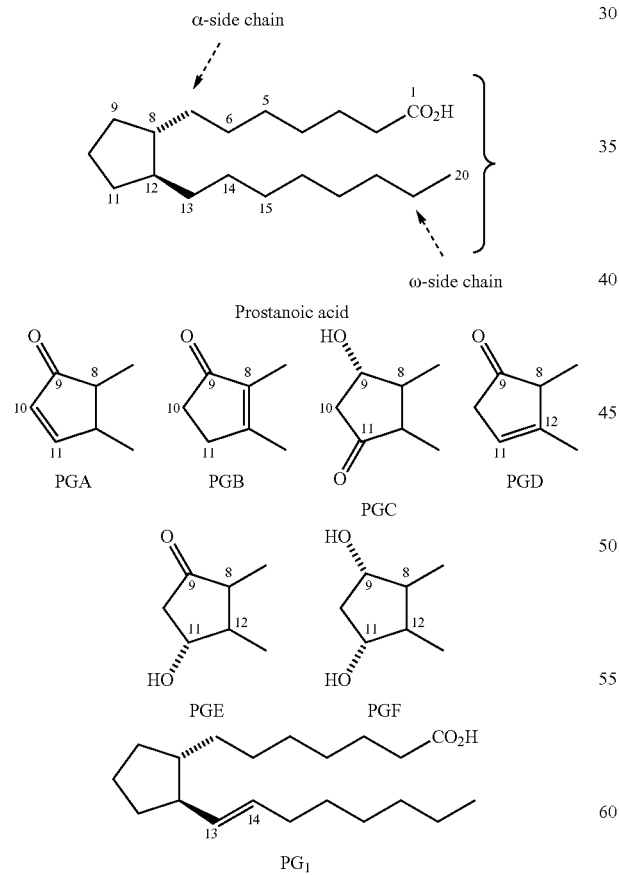

FIG. 1 - Prostaglandin nomenclature

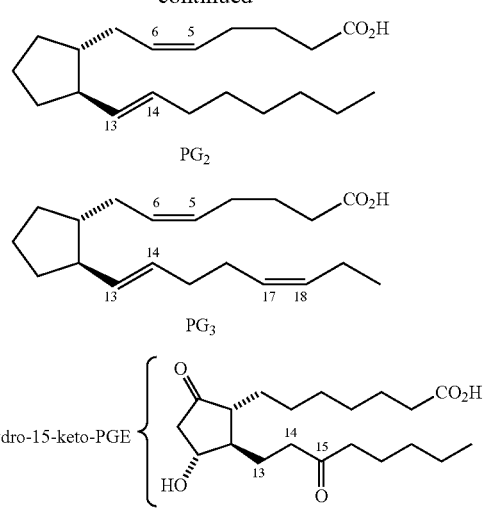

The existence of an electron deficient ketone at C15, along with a conveniently positioned hydroxyl group at C11 results in lubiprostone existing predominantly in a bicyclic form that includes a 6-membered hemiketal ring. This form exists in equilibrium with a monocyclic form (Scheme 1). Taken together, these two forms are referred to as tautomeric isomers. In sugar chemistry this kind of equilibrium of cyclic and acyclic forms is referred to as ring-chain tautomerisation (R-CT).[1] Whereas in $D_2O$, the ratio of the bicyclic form to monocyclic form is 6:1, in $CDCl_3$ it is 96:4.[2] Despite this tautomerisation and the predominance of the bicyclic hemiketal form, lubiprostone is still referred to as a 15-keto-prostaglandin E1 derivative. According to US2010056808A1 the two crystalline polymorphs of lubiprostone reported exist as the bicyclic form in the solid state.

[1] According to http://en.wikipedia.org/wiki/Tautomer, ring-chain tautomerisation "occurs when the movement of the proton is accompanied by a change from an open structure to a ring, such as the open chain and pyran forms of glucose."

[2] U.S. Pat. No. 7,355,064 B2.

Scheme 1 - "Ring-chain tautomer" forms of lubiprostone

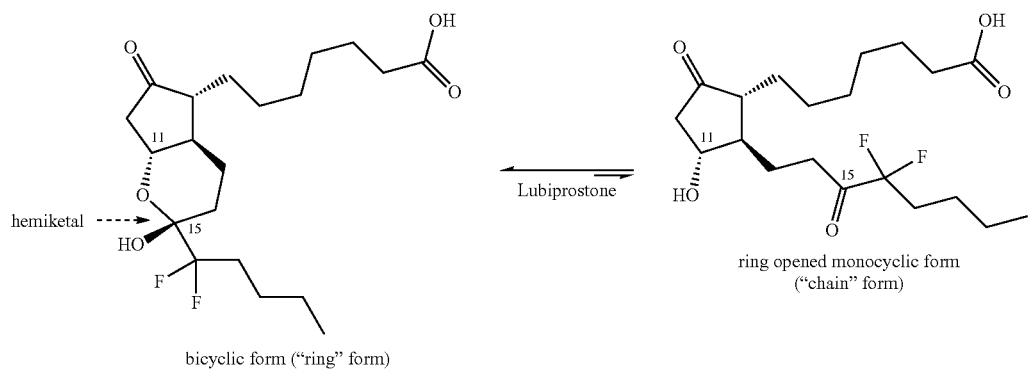

bicyclic form ("ring" form)

ring opened monocyclic form ("chain" form)

2. Related Art

An early approach with great versatility for the synthesis of prostaglandins and analogues was invented by E. J. Corey[3] in the late 60's and this is probably the strategy most used by industry. To date, besides the presently claimed process, it is the only method that has been disclosed for lubiprostone synthesis. This approach is referred to as the "Corey method". The Corey lactone aldehyde (a.k.a., Corey aldehyde),[4] which itself requires many synthetic steps, is central to the Corey approach and contains all of the three $PGE_1$ stereochemical centres (such as those required in lubiprostone) already in place, and the ω- and α-side chains are added sequentially by Horner-Wadsworth-Emmons (or HWE reaction) and Wittig reactions (Scheme 2). In the Corey approach, the order of addition of the α- and ω-side chains is interchangeable.

[3] *J. Am. Chem. Soc.*, 1969, 91, 5675-5676.
[4] *Angew. Chem. Int. Ed. Engl.*, 1991, 30, 455-465.

Scheme 2 - The "Corey method" for prostaglandin synthesis

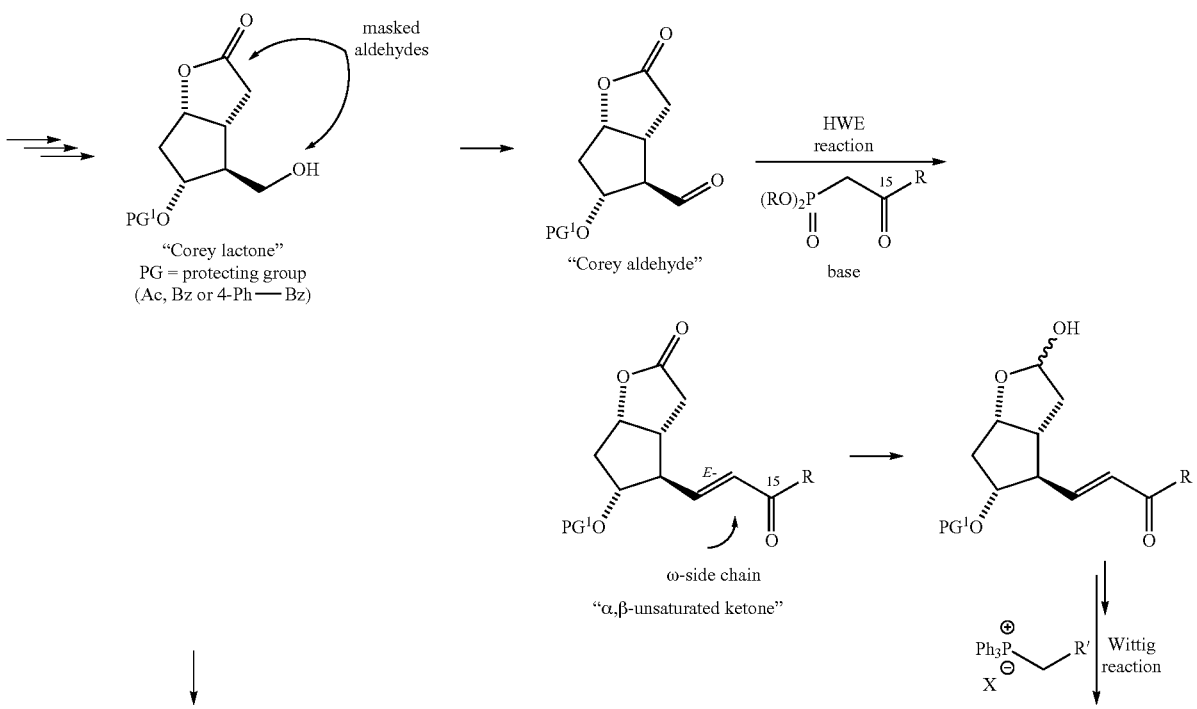

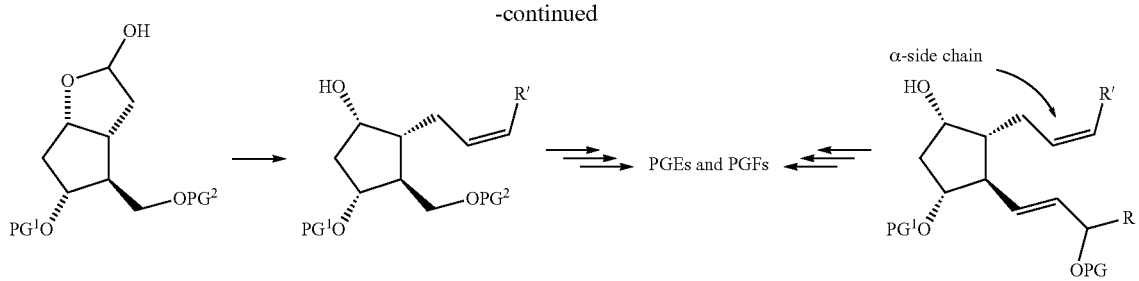

SUMMARY OF THE INVENTION

Prostaglandin Platform Technology of the Present Invention

Our company has previously developed the total syntheses of the prostaglandin analogues travoprost and bimatoprost. These synthetic routes and their processes were published in patent applications US20090259058A1 and WO2009141718A2 in 2009. The final steps in the syntheses of travoprost and bimatoprost are shown in Scheme 3 and pivot around a key 1,4-conjugate addition reaction (a.k.a., Michael addition) of a higher order cuprate, formed from compound (2A) or (2B), with cyclopentenone (1) (a diverging, common intermediate) to furnish the PGE$_2$s compound (3A) or (3B). Following this the two PGE$_2$s were converted into the PGF$_{2\alpha}$s compound (4A) or (4B) by stereoselective C9 ketone reduction. This was followed by double TBS deprotection (of C11-OTBS and C15-OTBS) to provide travoprost or the isopropyl ester analogue of bimatoprost, compound (5). The isopropyl ester was converted into bimatoprost by ester to amide exchange.

For lubiprostone, which is the subject of the present invention, we have utilised a different synthetic route since the structure of the API is significantly different from that of bimatoprost, and travoprost, however, the key intermediate compound (1) is still similarly utilised in a 1,4-conjugate addition of a cuprate compound. Thus, diverging intermediate (1) which we have a manufacturing process for, can still be used in lubiprostone synthesis.

Scheme 3 - The final steps in the synthesis of travosprost and bimatoprost using our prostaglandin platform technology (US20090259058A1 and WO2009141718A2).

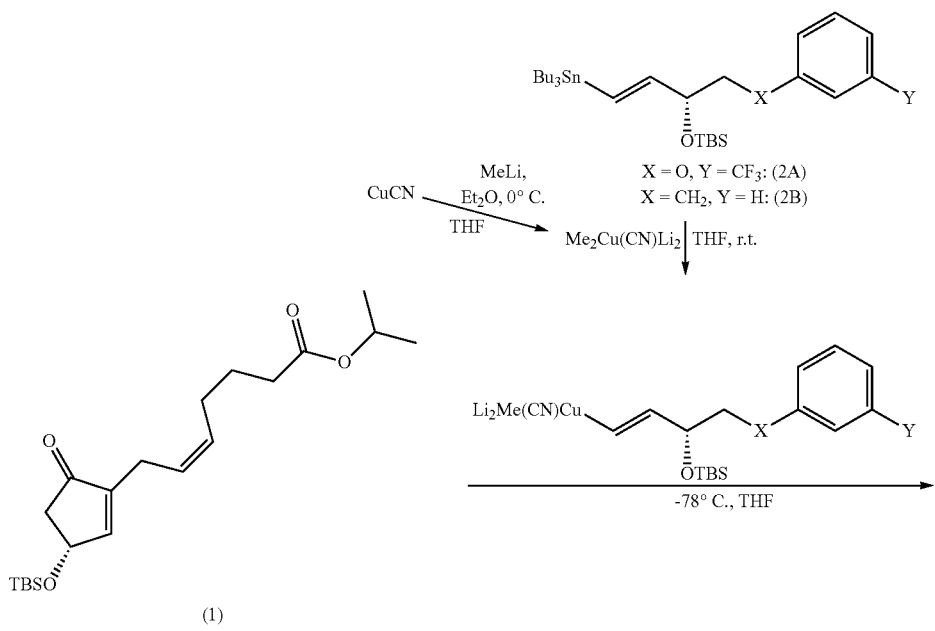

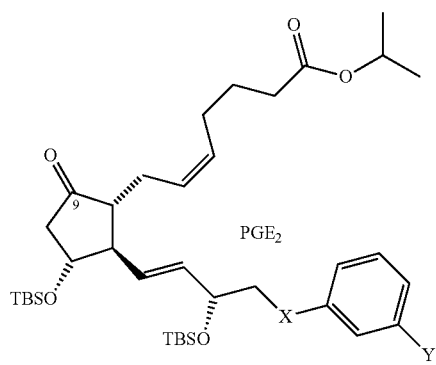

X = O, Y = CF₃: (3A)
X = CH₂, Y = H: (3B)

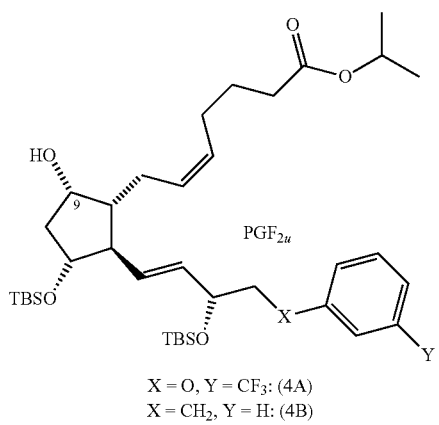

X = O, Y = CF₃: (4A)
X = CH₂, Y = H: (4B)

L-selectride
THF

X = O, Y = CF₃: TBAF, THF
X = CH₂, Y = H: aq. HF

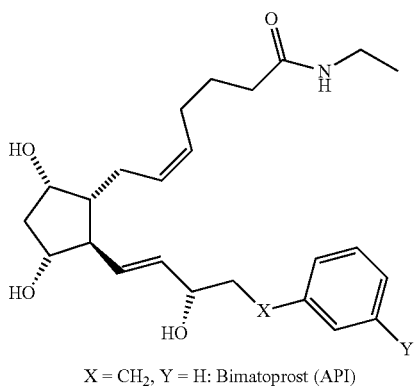

X = CH₂, Y = H: Bimatoprost (API)

aq. EtNH₂,
MeOH, 90° C.

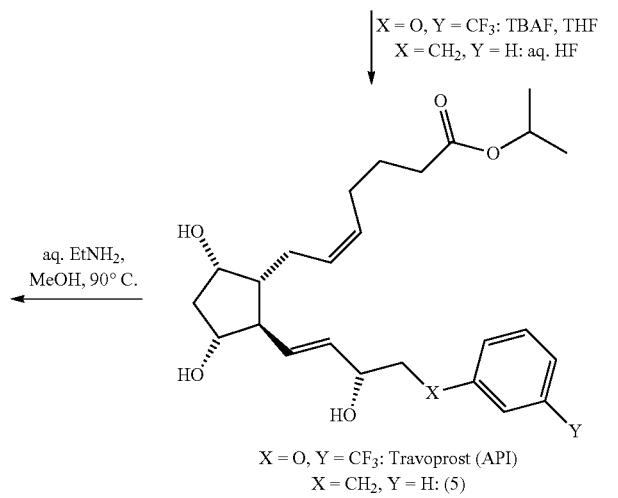

X = O, Y = CF₃: Travoprost (API)
X = CH₂, Y = H: (5)

Application of Prostaglandin Platform Technology to the Synthesis of Lubiprostone:

Our preferred synthesis of lubiprostone is shown in Scheme 4. We propose that the silyl protecting group can be selected from a range of analogues, but TBS is preferred. The α-side chain may possess a double bond between C5 and C6, and this may be cis- or trans- or a mixture of cis- and trans-, or C5 to C6 may be saturated. The C17 to C18 to C19 bonds can all be single C—C bonds, or can contain one double and one single bond. The existence of a double bond between C17 to C18, or C18 to C19 is only an artifact of the synthesis of H. The stereochemical configuration of C15 may be (R)- or (S)- and may be a mixture. The benzyl protecting group may be unsubstituted (i.e., $R^{14}$=H) or substituted (i.e., $R^{14}$=4-MeO, 2,4-DiMeO etc.). $R^{13}$ can be any substituent or combination of substituents that allows cuprate III to efficiently transfer its vinyl group to cyclopentenone I, but which itself does not react with cyclopentenone I. $R^{13}$ is preferably selected from the group of cyano, methyl and thienyl and combinations of these with lithium counter ions. Other organocopper reagents could also be conceivably used. Following the 1,4-conjugate addition (STEP 1c) of cuprate III and cyclopentenone I, all double bonds (C13, C14 and any others if present such as between C5 and C6, C17 and C18, and C18 and C19) of compound IV are removed along with the benzyl or substituted benzyl group (STEP 2) using a metal catalyst, preferably Pd, in a hydrogen atmosphere. Following this, the C15 alcohol of compound V is oxidised to a ketone using any suitable reagent, but preferably one (e.g., Pfitzner-Moffatt type oxidation reagents) that does not contaminate the product with metallic residues. The 15-keto prostaglandin VI, which is a doubly protected form of lubiprostone, is converted into lubiprostone, either by isopropyl ester hydrolysis to provide compound VII (STEP 4i), preferably accomplished by the aid of an enzyme, follow by desilylation to provide the isopropyl ester of lubiprostone (STEP 5i) using acid conditions or a fluoride reagent, or by desilylation (STEP 4ii) using acid conditions or a fluoride reagent followed by isopropyl ester hydrolysis (STEP 5ii), preferably accomplished by the aid of an enzyme.

$R^{11}$ of ester VIII can be alkyl, benzyl, aryl, but methyl and ethyl is preferred. $R^4$, $R^5$, $R^6$ may be any of alkyl, aryl, but all methyl is preferred. $R^7$ is H or $BnR^{14}$. $R^{15}$ may be $SnR^8R^9R^{10}$, Br, I, $ZrCp_2Me$ but is preferably $SnR^8R^9R^{10}$. $R^8$, $R^9$, $R^{10}$ may be any of alkyl, aryl, but all n-butyl is preferred. $R^{13}$ is nothing, Li(CN), Li₂(CN)Me, Li₂(CN)2-thienyl, Li(CH=CHCH(OBnR¹⁴)CF₂CHₙCHₘCHₒCH₃) (n, m and o is 1 or 2 such that either C17 through to C19 is fully saturated or C17 through to C19 contains one single and one double or triple bond), Li₂(CN)(CH=CHCH(OBnR¹⁴) CF₂CHₙCHₘCHₒCH₃) (n, m and o is 1 or 2 such that either C17 through to C19 is fully saturated or C17 through to C19 contains one single and one double or triple bond), but is preferably Li₂(CN)Me or Li₂(CN)2-thienyl.

Key aspects of this invention that are not before reported include the use of a 1,4-conjugate addition as a key step to form the prostaglandin backbone of lubiprostone in one single step from cyclopentenone I and higher order cuprate III. Following this, an efficient use of hydrogenation/hydrogenolysis is used to remove all of the double bonds of IV that are artefacts of IV's synthesis, as well as simultaneously removing the C15-O protecting group, to provide V. Another key aspect in the synthesis is the use of an enzyme to remove the ester protecting group. This is preferable because hydrolysis of the isopropyl ester using acidic or basic aqueous conditions leads to decomposition of the sensitive 15-keto-PGE structure, and would not be orthogonal as the silyl protecting group could also be removed thereby not providing us with synthetic control. The final two steps, which are deprotecting group steps, can be conducted in either order.

Of course other ester analogues (e.g., methyl, ethyl, propyl etc.) could be used in the synthesis of lubiprostone following the synthetic route of this invention, however, isopropyl is preferred.

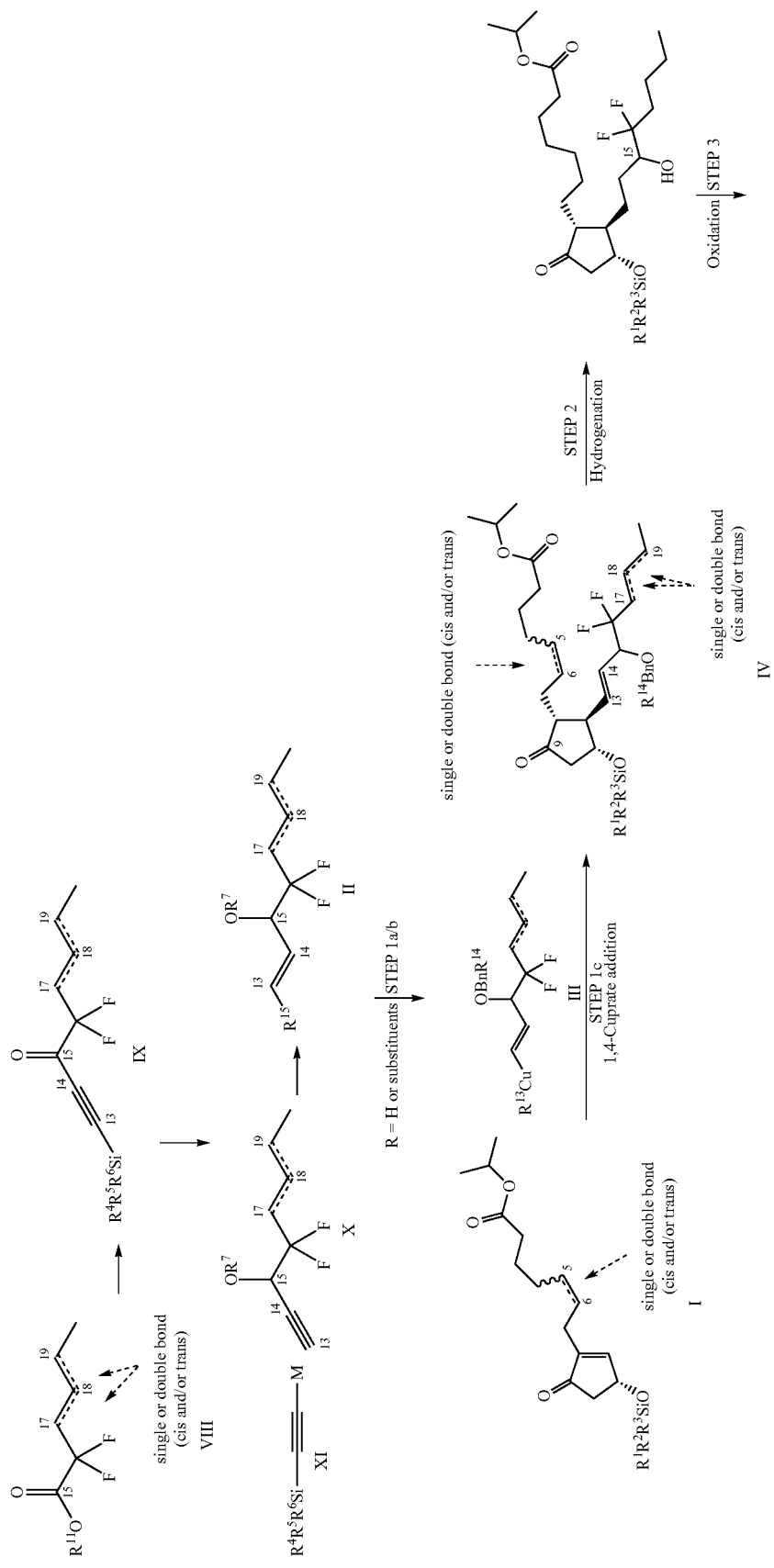
Scheme 4 - Summary of the preferred method for the synthesis of lubiprostone (the numberings show reflect the numbers of atoms as would be found in lubiprostone)

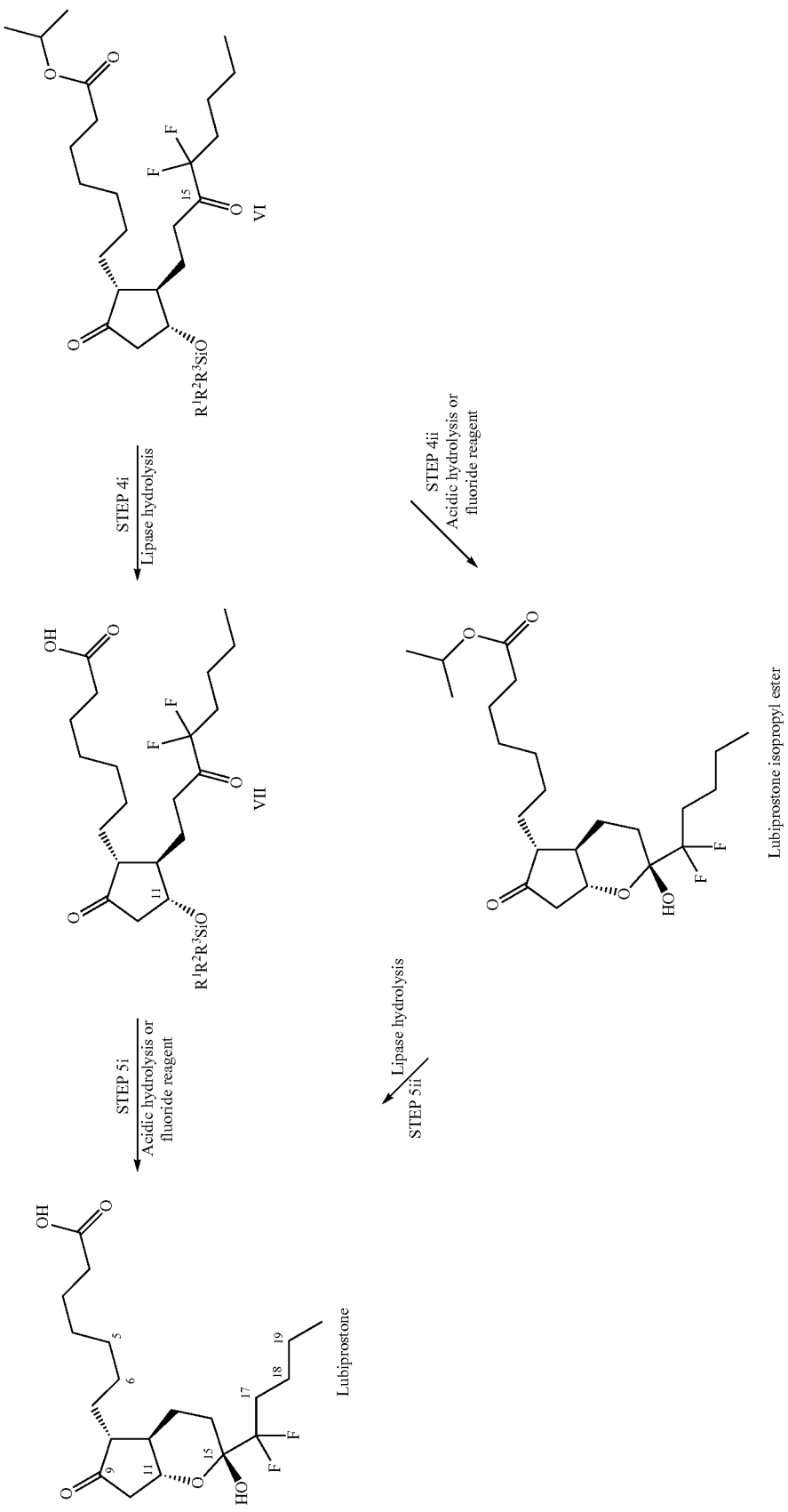

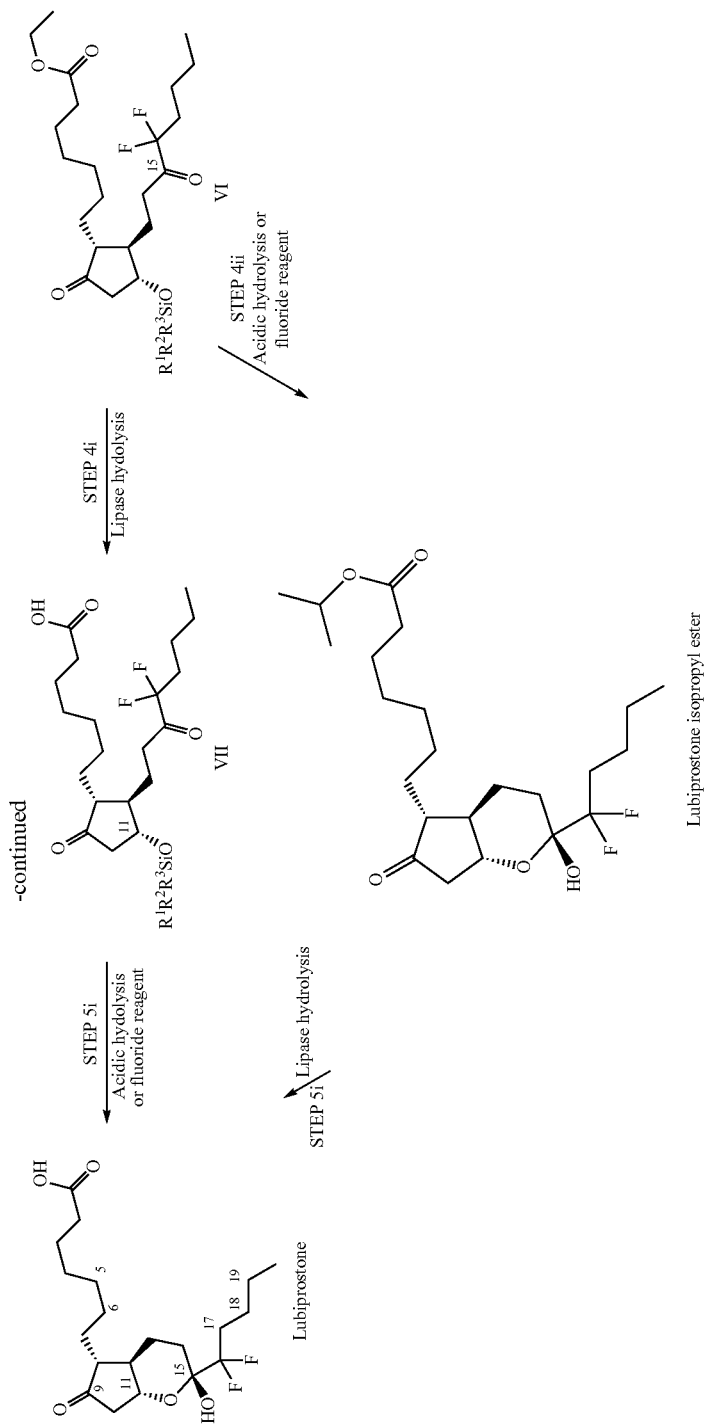

Accordingly, the present invention encompasses a new synthetic route to lubiprostone (Scheme 5), which involves 1,4-conjugate addition of a higher order cuprate compound Cu-IM7 (prepared in situ from IM7) to protected cyclopentenone (1) as a key step. We have also provided synthetic routes to IM7 (Scheme 7) and IM7b (Scheme 8) (and 4-methoxybenzyl derivatives IM7i and IM7bi), which are the starting materials for the w-side chain of lubiprostone. Unlike all the prior art syntheses of lubiprostone that we are aware of, we have utilised a silicon-based protecting group for the protection of the alcohol that ultimately becomes C11-O in lubiprostone. All other prior art methods that have been disclosed to our knowledge disclose the use of carbon based protecting groups such as THP. Also, unlike all of the other prior art methods that we are aware of, we prepared lubiprostone using a 1,4-conjugate addition approach, which differs greatly from the Corey method used in all the other prior art methods. This also sets our approach apart from all the other methods.

The synthetic route is discussed in detail below.

1)—Synthesis of Lubiprostone (Scheme 5):

Step 1:

The first step involves the 1,4-conjugate addition of higher order cuprate Cu-IM7 with key diverging intermediate (1) (STEP 1c) to provide the $PGE_2$ product (7). The higher order cuprate Cu-IM7 in that step was prepared in situ (STEP 1a) by the stepwise reaction of IM7 with MeLi to form the vinyl lithium derivative Li-IM7 followed by conversion (STEP 1b) to the higher order cuprate Cu-IM7 by reaction with an in situ prepared cuprate salt (MeCu(CN)Li) (also see Scheme 6). THF was preferred as the main solvent for this reaction step and the reaction was conducted at low temperatures (preferably below −30° C.).

In addition to the benzyl protecting group that is used to protected C15-OH (i.e., C3-OH of IM7), p-methoxybenzyl (a.k.a., 4-methoxybenzy) as a protecting group is also tested. Thus, STEP 1 was also tested using the p-methoxybenzyl derivative by conducting the 1,4-conjugate addition of higher order cuprate Cu-IM7i (prepared from the p-methoxybenzyl IM7 analogue, IM7i) with compound (1) to provide product p-methoxybenzyl ether (7i).

Step 2:

We conducted a global hydrogenation/hydrogenolysis in an organic solvent using a palladium catalyst supported on carbon in a hydrogen atmosphere which removed all three double bonds (C5-C6, C13-C14 and C17-C18) and the benzyl protecting group (or p-methoxybenzyl group when compound (7i) was used) simultaneously to provide compound (8). Although EtOAc was the preferred solvent, other solvents including EtOH could be used. An acid catalyst (such as p-TsOH) could also be used in the reaction.

Step 3:

The C15-OH was oxidized to provide the diketone (9) using the Swern oxidation method (i.e., $(COCl)_2$ with DMSO). Other oxidants, including pyridine sulfur trioxide complex/DMSO, can also be used.

Step 4i:

A range of enzymes that can catalyse the hydrolysis of esters (including Lipase PS IM, Lipase PS SD, PPL, PS IM) under a range of reaction conditions were found to be able to hydrolyse the isopropyl ester of compound (9) to provide its carboxylic acid form (10). A large range of organic solvents could be used including acetone, glycol, glycerol, DMSO. Typically the hydrolysis reaction was conducted at an elevated temperature (e.g., between 30-60° C.) and appropriate pH range. Commercially available Lipase PS SD was preferred when acetone was used as an organic solvent in conjunction with an aqueous buffer at an elevated temperature.

Step 5i:

Lubiprostone is prepared by TBS deprotection of the C11-OTBS of the compound (10) using mineral or organic acids such as $H_2SO_4$, HCl, TFA or fluoride reagents including TBAF and aq. HF in an organic solvent. $H_2SO_4$ in MeCN is preferred.

Alternatively the last two steps (i.e., STEP 4i and STEP 5i) can be conducted in reverse order with TBS deprotection (using an acid or fluoride reagent) in STEP 4ii followed by ester hydrolysis (using an ester hydrolysing enzyme in aqueous buffer/organic solvent) in STEP 5ii.

Lubiprostone can be converted into salt derivatives by reaction with bases, including nitrogen containing bases such as guanidine for example. These salts can possess different melting points and solubilities as compared to that of lubiprostone thereby providing access to alternative methods by which lubiprostone can be purified. We provide a simple method to form the guanidine salt of lubiprostone.

Scheme 5 - Synthesis of lubiprostone.

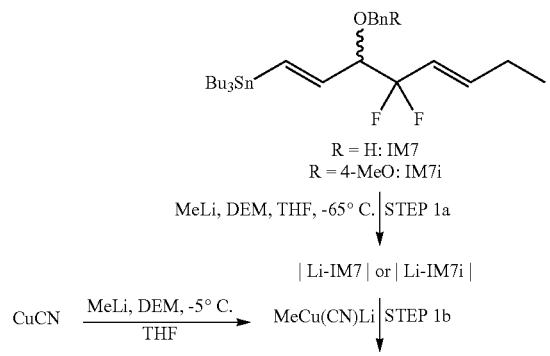

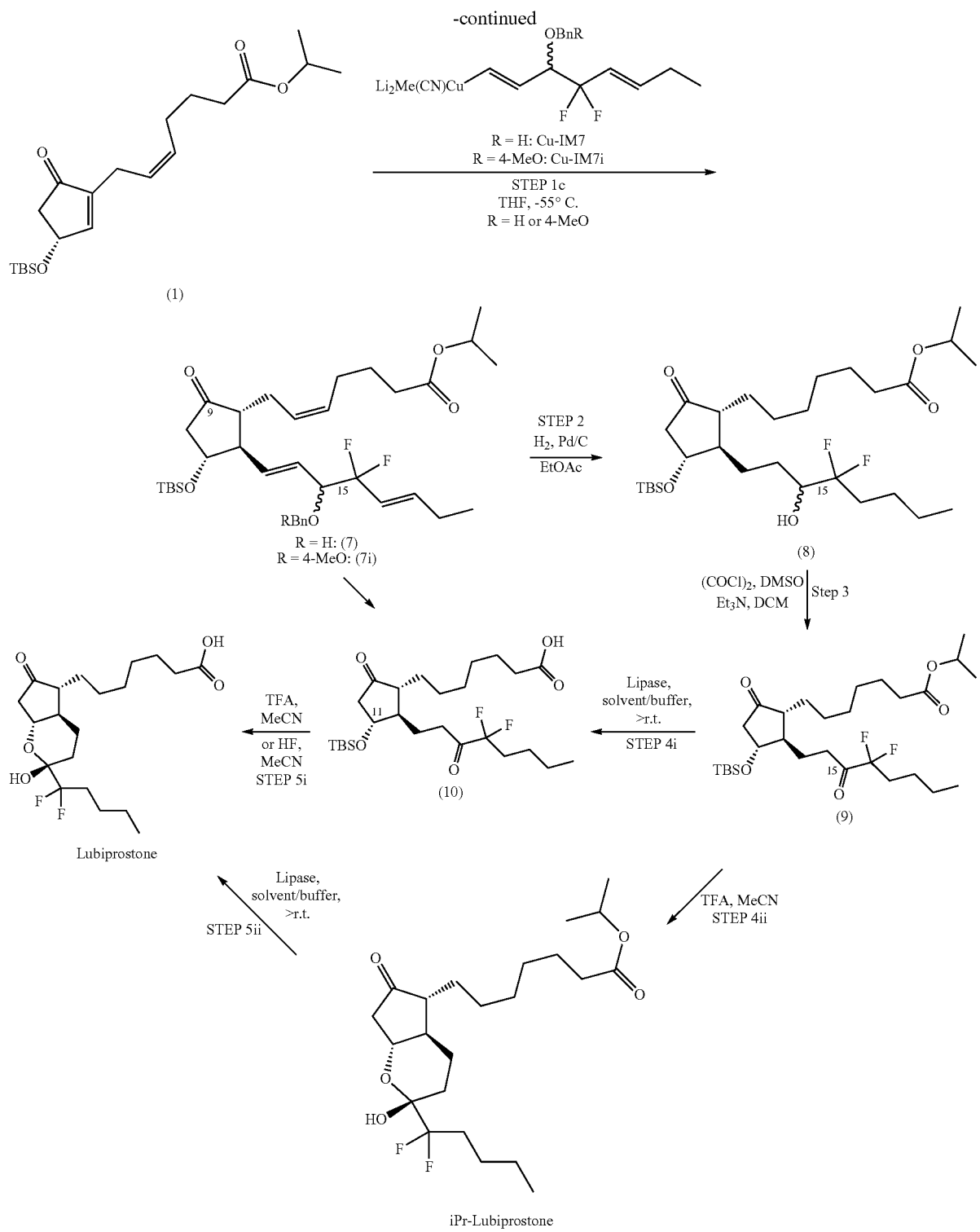

2) Synthesis of the ω-Side Chain:

Lubiprostone is prepared by the 1,4-conjugate addition of a higher order cuprate (Cu-IM7, Cu-IM7b, Cu-IM7i or Cu-IM7bi) with the compound (1) to form a PGE$_2$ compound. The higher order cuprate Cu-IM7 (or Cu-IM7b, Cu-IM7i or Cu-IM7bi) is prepared from trans-vinyl stannane IM7 (or IM7i, IM7b, or IM7bi) as shown in Scheme 6. The methyl dummy ligand can be substituted with a 2-thienyl group by the use of the commercially available lower order cuprate salt 2-thienyl(cyano)copper lithium in STEP 1b to provide Th—Cu-IM7, in place of methyl(cyano)copper lithium (MeCu(CN)Li).

Scheme 6 - Synthesis of requisite higher order cuprate required in 1,4-conjugate addition with the compound (1)

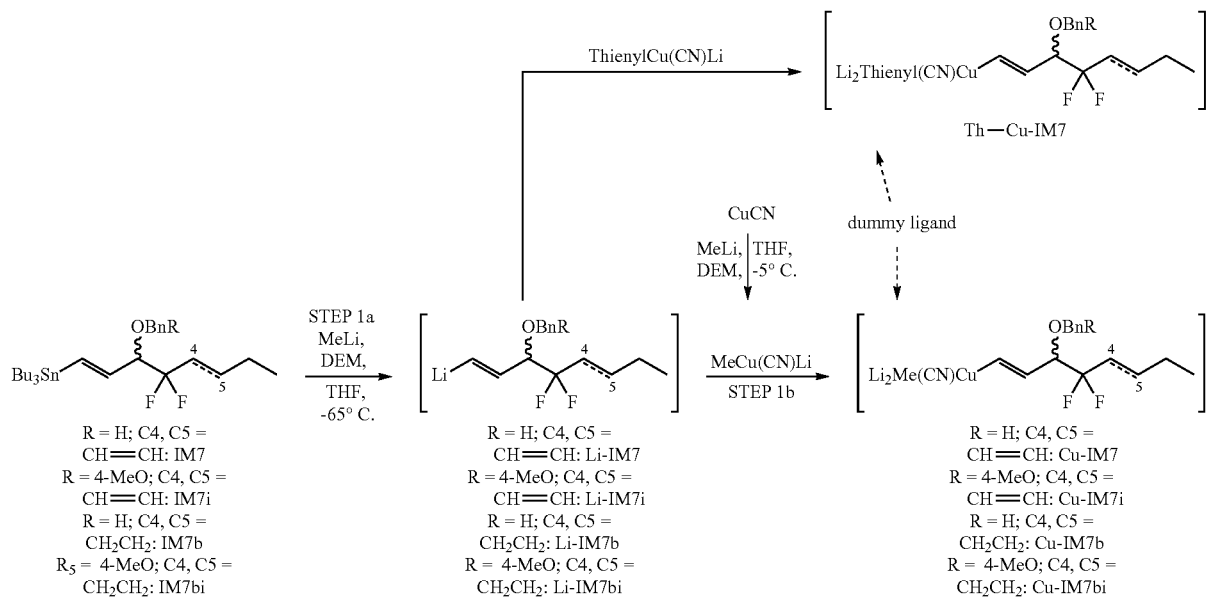

We prepared the requisite trans-vinyl stannane IM7 (or IM7i) using the process as shown in Scheme 7. Cheap and commercially available SM1 was converted in situ to its organozinc bromide derivative and was reacted with cheap and commercially available butanal to provide alcohol IM1. This was preferably conducted in THF and the addition of Lewis acids could be beneficial. Removal of the C3-oxygen was achieved by its conversion to triflate IM2, followed by elimination promoted by bases including DBU to furnish IM3. The existence of the double bond in IM3 is of no consequence and Scheme 8). Following its synthesis, IM3 was converted into the acyl acetylene IM4 which was reduced and desilylated in one-pot to provide propargyl alcohol IM5. Thus, IM5 was treated with $Bu_3SnH$ in the presence of the radical initiator AIBN to provide De-Bn-IM7, which was then O-protected with benzyl bromide under basic conditions (e.g., NaH or t-BuONa, the former was preferred) to furnish IM7. Alternatively, C3-OH of IM5 could be protected and the product IM6 then stannylated to give IM7.

Scheme 7 - Synthesis of IM7 as required for the higher order cuprate Cu-IM7

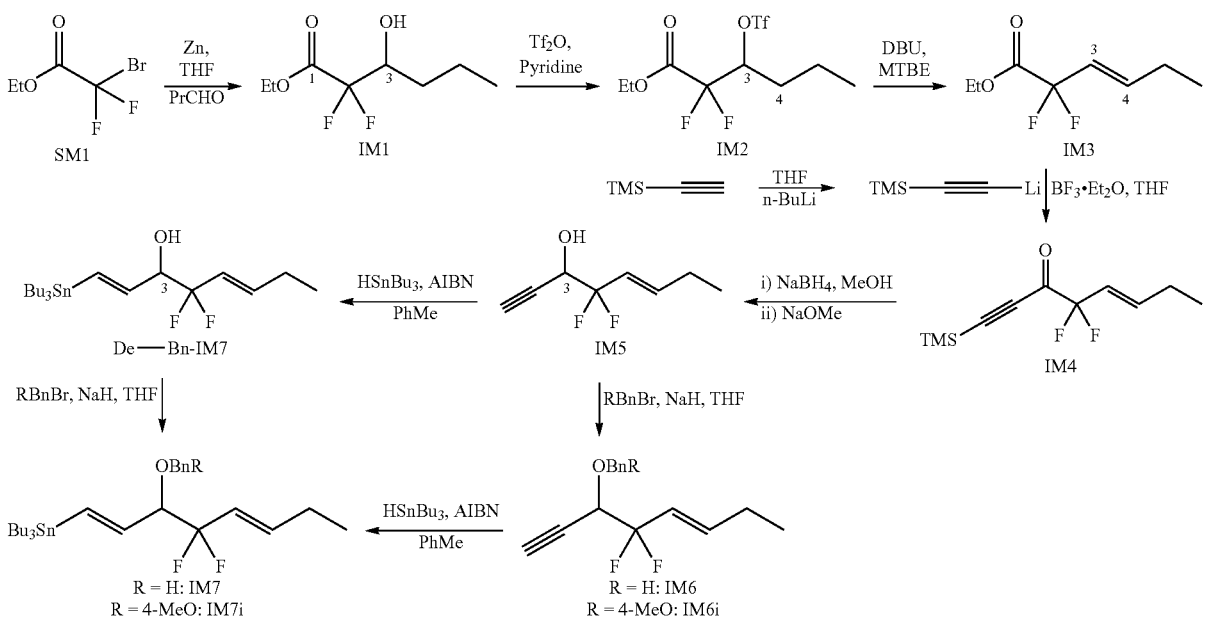

lubiprostone can be synthesized from either IM3 or IM3b (see

As mentioned above, the IM3 analogue ethyl 2,2-difluorohexanoate (IM3b) is commercially available. Using the same synthetic sequence as described in Scheme 7, IM3b was converted it into IM7b (Scheme 8).

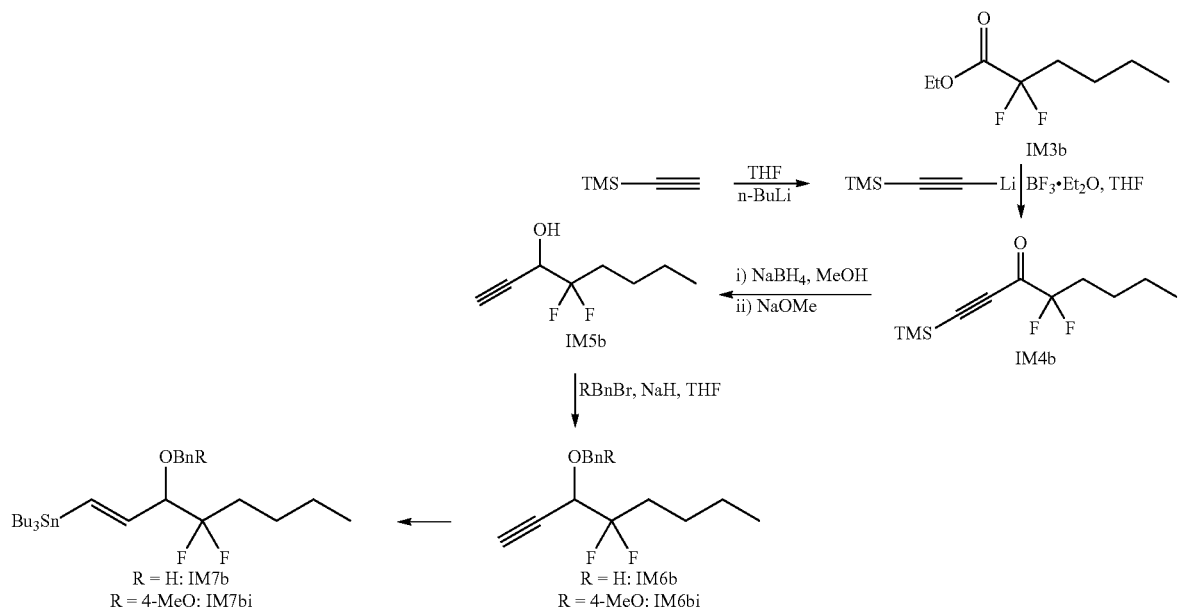

Scheme 8 - Synthesis of IM7b as required for the higher order cuprate Cu-IM7b

EXAMPLES

Example 1

Step 1: Synthesis of IM1 (Ethyl 2,2-difluoro-3-hydroxyhexanoate)

To a mechanically stirred mixture of zinc (108 g, 1.66 mol), n-butanal (100 g, 1.39 mol), CeCl$_3$.7H$_2$O (10.14 g, 0.027 mol) and anhydrous THF (1.3 L) at about 25° C. was added ethyl 2-bromo-2,2-difluoroacetate (SM1, 33.8 g, 0.167 mol) under N$_2$. The mixture was stirred at about 25° C. until the reaction had initiated, then SM1 (304 g, 1.50 mol) was added dropwise at 35° C. without external heating. After the addition completed, the mixture was stirred at 20~35° C. until n-butanal was less than 2.0%. The reaction mixture was then cooled to about 5° C. and sat. aq. NH$_4$Cl (800 mL) was added slowly at about 5° C., and then adjust pH 3.0 with 6 N HCl. The mixture was stirred for 15 min. and then filtered through a plug of celite; the filter cake was washed once with MTBE (1 L). The combined filtrate was then separated and the aqueous layer was extracted once with MTBE (1 L). The combined organic layers were washed once with sat. aq. NaHCO$_3$ (1 L), once with sat. aq. NH$_4$Cl (1 L) and then concentrated at <50° C. under reduced pressure to give 281 g of crude IM1 with 80% GC purity. The crude IM1 was purified by vacuum distillation to provide 160 g IM1 with 98% GC purity in 58% GC total yield.

$^1$H NMR (300 MHz, CDCl$_3$): δ 4.36 (q, J=7.1 Hz, 2H), 4.10-3.98 (m, 1H), 1.68-1.58 (m, 2H), 1.57-1.40 (m, 2H), 1.37 (t, J=7.1 Hz, 3H), 0.97 (t, J=7.1 Hz, 3H)

m/z (GC-MS): 197 ([MH]$^+$, 1), 124 (75), 96 (100), 73 (45), 55 (80)

Example 2

Step 2 Synthesis of IM2 (ethyl 2,2-difluoro-3-(trifluoromethylsulfonyloxy)hexanoate)

To a mechanically stirred solution of IM1 (3 g, 0.015 mol) and pyridine (1.42 g, 0.018 mol) in anhydrous DCM (6 mL) at 0-5° C. was added a mixture of Tf$_2$O (4.53 g, 0.016 mol) in anhydrous DCM (3 mL) dropwise at 0-15° C. under N$_2$. The mixture was stirred at 5-15° C. until IM1 was less than 2.0%. Then water (9 mL) was added and the resulted mixture was separated. The aqueous layer was extracted once with DCM (9 mL) and the combined organic layer was washed once with 5% aq. HCl (9 mL), once with sat. aq. NaHCO$_3$ (9 mL) and once with brine (9 mL) and then concentrated at <45° C. under reduced pressure to give 4.2 g of crude IM2 with 96% GC purity $^1$H NMR (300 MHz, CDCl$_3$): $^1$H NMR (300 MHz, CDCl$_3$) δ 5.21 (m, 1H), 4.40 (q, J=7.2 Hz, 2H), 2.00-1.74 (m, 2H), 1.70-1.43 (m, 2H), 1.39 (t, J=7.2 Hz, 3H), 1.00 (t, J=7.3 Hz, 3H)

m/z (GC-MS): 329 ([MH]$^+$, 1), 151 (20), 124 (15), 106 (70), 77 (100), 69 (45), 55 (55)

Example 3

Step 3 Synthesis of IM3 (ethyl 2,2-difluorohex-3-enoate)

To a mechanically stirred flask was added IM2 (300 g, 0.91 mol) and DBU (165 g, 1.08 mol) in anhydrous MTBE (900 mL), the mixture was heated to reflux with stirring until IM2 was less than 3.0%. The reaction mixture was then cooled to 0~10° C. followed by adding of 5% aq. HCl (900 mL). The resulted solution was separated and the aqueous layer was extracted once with MTBE (900 mL). The combined organic layer was washed once with sat. aq. NaHCO$_3$ (900 mL), once with brine (900 mL), dried with anhydrous MgSO$_4$ and then concentrated at <45° C. under reduced pressure to give 167 g of crude IM3. The crude IM3 was purified by vacuum distillation to give 125 g IM3 with 85% GC purity in 66% GC yield based on IM1

$^1$H NMR (300 MHz, CDCl$_3$): δ 6.33 (dtt, J=11.5, 6.2, 2.6 Hz, 1H), 5.75-5.58 (m, 1H), 4.32 (q, J=7.1 Hz, 2H), 2.24-2.11 (m, 2H), 1.35 (t, J=7.1 Hz, 3H), 1.05 (t, J=7.4 Hz, 3H)

m/z (GC-MS): 179 ([MH]$^+$, 4), 106(65), 77 (100), 55 (20)

Example 4

Step 4 Synthesis of IM4 (4,4-difluoro-(trimethylsilyl)oct-5-en-1-1-3-one)

To a mechanically stirred solution of TMS-acetylide (182 g, 1.85 mol) in anhydrous THF (880 mL) at 0-10° C. was added a solution of n-BuLi (2.5 mol/L, 748 mL, 1.87 mol) dropwise at 0-10° C. under N$_2$. The reaction mixture was stirred at this temperature for 1 h. To a mechanically stirred flask was added IM3 (220 g, 1.23 mol, 1.0 eq., 92% GC purity) and BF$_3$/Et$_2$O (264 g, 1.86 mol) in anhydrous THF (220 mL) under N$_2$. The solution was cooled to −70~−78° C. and then TMS-acetylene-lithium solution was added at −60~−78° C. in 2 h. The reaction solution was stirred at −70~−78° C. until IM3 disappeared. Sat. aq. NH$_4$Cl (1.1 L) was added slowly into the reaction, the temperature was allowed to warm to 0~10° C. The mixture was then extracted once with EtOAc (550 mL) and then separated; the aqueous layer was extracted once with EtOAc (550 mL). The combined organic layer was washed once with water (660 mL) and once with brine (660 mL) and then concentrated at <55° C. under reduced pressure to give 297 g of crude IM4 with 87% GC purity.

$^1$H NMR (300 MHz, CDCl$_3$): $^1$H NMR (300 MHz, CDCl$_3$) δ 6.37 (dtt, J=11.3, 6.3, 2.5 Hz, 1H), 5.69-5.52 (m, 1H), 2.26-2.13 (m, 2H), 1.06 (t, J=7.4 Hz, 3H), 0.28 (s, 9H)

m/z (GC-MS): 231 ([MH]$^+$, 1), 125 (100), 97 (35), 73 (30)

Example 5

Step 5 Synthesis of IM5 (4,4-difluorooct-5-en-1-yn-3-ol)

To a solution of IM4 (321 g, 1.4 mol) in MeOH (1.5 L) at 0~−5° C. was added solid NaBH$_4$ (19.6 g, 0.7 mol) slowly. The reaction solution was stirred at this temperature until IM4 consumed. Then solid NaOMe (37.7 g, 0.7 mol) was added and the reaction solution was stirred at this temperature until TMS-IM5 consumed. Sat. aq. NH$_4$Cl (1 L) and H$_2$O (1 L) was added and then the mixture was adjusted to pH 5~6 with 6 M HCl, the mixture was then extracted three times with MTBE (600 mL each). The combined organic layer was washed once with water (600 mL), once with brine (600 mL) and then concentrated at <45° C. under reduced pressure to give 224 g of crude IM5 with 87% GC purity.

$^1$H NMR (300 MHz, CDCl$_3$): δ 6.32 (dtd, J=10.8, 6.1, 2.3 Hz, 1H), 5.78-5.59 (m, 1H), 4.57-4.46 (m, 1H), 2.55 (d, J=2.2 Hz, 1H), 2.26-2.12 (m, 2H), 1.06 (t, J=7.4 Hz, 3H)

m/z (GC-MS): 159 ([M−H]$^+$, 1), 105 (5), 77 (100), 55 (30)

Example 6

Step 6 Synthesis of De-Bn-IM7 ((1E)-4,4-difluoro-1-(tributylstannyl)octa-1,5-dien-3-ol)

To the hot (70° C.) solution of IM5 (110 g, 0.68 mol) in toluene (550 mL) was added Bu$_3$SnH (219 g, 0.75 mol) and AIBN (12.4 g, 0.075 mol) with stirring, the mixture was stirred at 80~85° C. until IM5 consumed. The reaction mixture was evaporated at <55° C. to give 338 g crude De-Bn-IM7. The crude De-Bn-IM7 was purified by column chromatography providing 82.5 g of De-Bn-IM7 with 91% GC purity and 111.5 g mixture of cis-De-Bn-IM7 and De-Bn-IM7.

$^1$H NMR (300 MHz, CDCl$_3$): δ 6.48-6.40 (m, 1H), 6.27-6.13 (m, 1H), 6.01 (dd, J=19.3, 5.1 Hz, 1H), 5.55 (dtt, J=15.4, 11.9, 1.7 Hz, 1H), 4.34-4.22 (m, 1H), 2.20-2.11 (m, 2H), 1.55-1.43 (m, 6H), 1.30 (dq, J=14.0, 7.1 Hz, 6H), 1.03 (t, J=7.4 Hz, 3H), 0.90 (dd, J=14.5, 7.3 Hz, 15H)

m/z (ES-API, Neg): 451, 495 (M+HCOO$^−$)

Example 7

Step 7 Synthesis of IM7 (((1E,5E)-3-(benzyloxy)-4,4-difluoroocta-1,5-dienyl)tributylstannane)

To a mechanically stirred mixture of NaH (4.0 g, 60%, 0.1 mol) in DMF (170 mL) was added a solution of De-Bn-IM7 (42 g, 93.1 mmol) in DMF (20 mL) at −10~0° C., the reaction mixture was stirred at this temperature for 1 h, a solution of BnBr (16.7 g, 97.7 mmol) in DMF (20 mL) was added dropwise into the reaction mixture at −10~0° C. until De-Bn-IM7 consumed. Water (210 mL) was added and the mixture was extracted twice with MTBE (210 mL each). The combined organic layer was washed once with sat. aq. NH$_4$Cl (210 mL), once with water (210 mL) and once with brine (210 mL) and then concentrated at <45° C. under reduced pressure to give 52.3 g of crude IM7 with 91.1% HPLC purity.

$^1$H NMR (300 MHz, CDCl$_3$): δ 7.39-7.26 (m, 5H), 6.38 (d, J=19.2 Hz, 1H), 6.19-6.09 (m, 1H), 5.88 (dd, J=19.2, 6.8 Hz, 1H), 5.60 (dtt, J=15.4, 11.9, 1.7 Hz, 1H), 4.69 (d, J=12.2 Hz, 1H), 4.51 (d, J=12.2 Hz, 1H), 3.94-3.87 (m, 1H), 2.20-2.06 (m, 2H), 1.57-1.43 (m, 6H), 1.32 (dt, J=15.0, 7.4 Hz, 6H), 1.02 (t, J=7.4 Hz, 3H), 0.91 (q, J=7.5 Hz, 15H)

m/z (EI): 581 ([M+K$^+$], 100), 565 ([M+Na$^+$], 60)

Example 8

Step 8 Synthesis IM7i of (((1E,5E)-3-(benzyloxy)-4,4-difluoroocta-1,5-dienyl)tributylstannane)

To a mechanically stirred mixture of NaH (0.49 g, 60%, 0.012 mol) in DMF (20 mL) was added a solution of De-Bn-IM7 (5 g, 0.011 mol) in DMF (2.5 mL) at −10~0° C., the reaction mixture was stirred at this temperature for 1 h, a solution of 1-(bromomethyl)-4-methoxybenzene (2.34 g, 0.0116 mol) in DMF (2.5 mL) was added dropwise into the reaction mixture at −10~0° C. until De-Bn-IM7 consumed. Water (25 mL) was added and the mixture was extracted twice with MTBE (25 mL each). The combined organic layer was washed once with sat. aq. NH$_4$Cl (25 mL), once with water (25 mL) and once with brine (25 mL) and then concentrated at <45° C. under reduced pressure to give 6.3 g of crude IM7i. The crude IM7i was purified by column chromatography providing 4.2 g of IM7i with 92% GC purity in 64% HPLC yield.

$^1$H NMR (300 MHz, CDCl$_3$): δ 7.25 (d, J=8.6 Hz, 2H), 6.87 (d, J=8.6 Hz, 2H), 6.42-6.31 (m, 1H), 6.13 (d, J=15.8 Hz,

1H), 5.87 (dd, J=19.2, 6.7 Hz, 1H), 5.58 (dd, J=26.5, 13.2 Hz, 1H), 4.62 (d, J=11.8 Hz, 1H), 4.44 (d, J=11.8 Hz, 1H), 3.94-3.87 (m, 1H), 2.20-2.06 (m, 2H), 1.57-1.43 (m, 6H), 1.32 (dt, J=15.0, 7.4 Hz, 6H), 1.02 (t, J=7.4 Hz, 3H), 0.91 (q, J=7.5 Hz, 15H)

m/z (ES API, Pos): 611 ([M+K$^+$], 100), 595 ([M+Na$^+$], 70)

Example 9

Step 9 Synthesis of IM6 ((E)-((4,4-difluorooct-5-en-1-yn-3-yloxy)methyl)benzene)

To a mechanically stirred mixture of IM5 (100 g, 76% GC purity, 0.62 mol) and t-BuOK (71.4 g, 0.74 mol) in THF (300 mL) was added a solution of BnBr (116 g, 0.68 mol) in THF (200 mL) at 60~70° C., the reaction mixture was stirred at this temperature for 1 h until IM5 was less than 5%. The mixture was cooled to 15~30° C., water (1 L) and MTBE (1 L) was added and the mixture was stirred for 15 min., the aqueous layer was extracted once with MTBE (500 mL). The combined organic layer was washed once with sat. aq. NH$_4$Cl (500 mL) and once with brine (500 mL) and then concentrated at <45° C. under reduced pressure to give 155 g of crude IM6 with 61% HPLC purity. The crude IM6 was purified by column chromatography providing 86 g of IM6 with 86% GC purity in 62% GC yield.

$^1$H NMR (300 MHz, CDCl$_3$): δ 7.37-7.31 (m, 5H), 6.35-6.22 (m, 1H), 5.78-5.61 (m, 1H), 4.86 (d, J=12.0 Hz, 1H), 4.64 (d, J=12.0 Hz, 1H), 4.29 (dt, J=8.0, 2.2 Hz, 1H), 2.55 (d, J=8.0, 2.1 Hz, 1H), 2.22-2.09 (m, 2H), 1.02 (t, J=7.4 Hz, 3H)

Example 10

Step 10 Synthesis of IM7

To the hot (80° C.) solution of IM6 (69 g, 86%, 0.28 mol) in toluene (340 mL) was added Bu$_3$SnH (88 g, 0.30 mol) and AIBN (5.1 g, 0.03 mol) under stirring. The mixture was stirred at 80~85° C. until IM6 consumed. The reaction mixture was evaporated at <55° C. to give 150 g crude IM7. The crude IM7 was purified by column chromatography providing 75 g of IM7 with 61.2% GC purity in 65% GC yield.

Step 1: Synthesis of Compound (7)

(Z)-isopropyl7-((1R,2R,3R)-2-((1E,5E)-3-(benzyloxy)-4,4-difluoroocta-1,5-dienyl)-3-(tert-butyldimethyl-silyloxy)-5-oxocyclopentyl)hept-5-enoate)

Example 11

To a mixture of CuCN (26.7 g, 0.3 mol) in THF (375 mL) at −10~0° C. was added a solution of MeLi in diethoxymethane (91 mL, 3 M, 0.27 mol) dropwise under N$_2$. The reaction mixture was stirred at this temperature for 0.5 h. To a solution of IM7 (147 g, 90% HPLC purity, 0.27 mol) in THF (750 mL) at −60~70° C. was added a solution of MeLi in diethoxymethane (91 mL, 3 M, 0.27 mol) dropwise under N$_2$. The reaction mixture was stirred at this temperature until IM7 was consumed. The prepared MeCu(CN)Li solution was added dropwise into the reaction at −40~−50° C. for another 0.5 h. Solution of compound (1) (82.7 g, 0.22 mol) in THF (375 mL) was then added dropwise into the former reaction solution at −50~−60° C. The reaction mixture was stirred at this temperature until the reaction completed. Sat. aq. NH$_4$Cl (750 mL) was added at this temperature and the resulted mixture was then warmed to r.t and filtered, the filter cake was washed once with MTBE (750 mL). The filtrate was separated and the aqueous layer was extracted once with MTBE (375 mL). The combined organic layer was washed once with brine (750 mL) and then concentrated at <55° C. under reduced pressure to give 228 g of crude compound (7), it was purified by column chromatography providing 107 g of compound (7) with 90% HPLC purity in 70% yield based on the compound (1).

Example 12

To a solution of IM7 (5 g, 9.2 mmol) in THF (30 mL) at −60~−70° C. was added a solution of MeLi in diethoxymethane (3.1 mL, 3 M, 9.3 mmol) dropwise under N$_2$. The reaction mixture was stirred at this temperature until IM7 consumed. Lithium 2-thienylcyanocuprate (37 mL, 0.25 M, 9.25 mmol) was added dropwise under N$_2$. The reaction mixture was stirred at this temperature for 1 h. Solution of compound (1) (2.8 g, 7.4 mmol) in THF (20 mL) was then added dropwise into the former reaction solution at −50~−60° C. The reaction mixture was stirred at this temperature until the reaction completed. Sat. aq. NH$_4$Cl (15 mL) was added at this temperature and the resulted mixture was then warmed to r.t. and filtered, the filter cake was washed once with EtOAc (25 mL). The filtrate was separated and the aqueous layer was extracted once with EtOAc (25 mL). The combined organic layer was washed once with brine (25 mL) and then concentrated at <55° C. under reduced pressure to give 8.2 g of crude compound (7) with 29.5% HPLC purity in 51.8% HPLC yield based on compound (1).

$^1$H NMR (300 MHz, CDCl$_3$): δ 7.39-7.27 (m, 5H), 6.24-6.10 (m, 1H), 5.81-5.69 (m, 1H), 5.68-5.50 (m, 2H), 5.49-5.27 (m, 2H), 4.99 (dt, J=12.5, 6.3 Hz, 1H), 4.68 (dd, J=12.0, 3.0 Hz, 1H), 4.52 (dd, J=12.0, 5.9 Hz, 1H), 4.14-4.04 (m, 1H), 4.04-3.92 (m, 1H), 2.74-2.66 (m, 1H), 2.65-2.51 (m, 2H), 2.49-2.28 (m, 2H, H8), 2.28-1.96 (m, 5H), 1.75-1.58 (m, 2H), 1.30-1.23 (m, 2H), 1.21 (d, J=6.3 Hz, 6H), 1.03 (t, J=7.4 Hz, 3H), 0.88 (s, 9H), 0.05 (dd, J=5.9, 3.4 Hz, 6H)

m/z (API-ES, Pos): 655 ([M+Na$^+$], 100)

Example 13

Step 1: Synthesis of Compound (7i)

((Z)-isopropyl7-((1R,2R,3R)-3-(tert-butyldimethylsilyloxy)-2-((1E,5E)-4,4-difluoro-3-(4-methoxybenzyloxy)octa-1,5-dienyl)-5-oxocyclopentyl)hept-5-enoate)

To a mixture of CuCN (0.77 g, 8.5 mmol) in THF (10 mL) at −10~0° C. was added a solution of MeLi in diethoxymethane (2.6 mL, 3 M, 7.8 mmol) dropwise under N$_2$. The reaction mixture was stirred at this temperature for 0.5 h. To a solution of IM7i (4.1 g, 92% HPLC purity, 7.8 mmol) in THF (20 mL) at −60~−70° C. was added a solution of MeLi in diethoxymethane (2.6 mL, 3 M, 7.8 mmol) dropwise under N$_2$. The reaction mixture was stirred at this temperature until IM7i consumed. The prepared MeCu(CN)Li solution was added dropwise into the reaction at −40~−50° C. for another 0.5 h. Solution of compound (1) (2.37 g, 6.2 mmol) in THF (10 mL) was then added dropwise into the former reaction solution at −50~−60° C. The reaction mixture was stirred at this temperature until the reaction completed. Sat. aq. NH$_4$Cl (20 mL) was added at this temperature and the resulted mixture was then warmed to r.t. and filtered, the filter cake was washed once with MTBE (20 mL). The filtrate was separated and the aqueous layer was extracted once with MTBE (10 mL). The combined organic layer was washed once with brine (20 mL) and then concentrated at <55° C. under reduced pressure to give 6.8 g of crude compound (7i), it was purified by column chromatography providing 2.3 g of compound (7i) with 88.6% HPLC purity in 51 HPLC yield based on compound (1).

$^1$H NMR (300 MHz, CDCl$_3$): δ 7.26-7.20 (m, 2H), 6.91-6.83 (m, 2H), 6.25-6.08 (m, 1H), 5.72 (ddd, J=17.3, 12.8, 4.8 Hz, 1H), 5.65-5.50 (m, 2H), 5.49-5.28 (m, 2H, H5), 4.99 (dt, J=12.5, 6.3 Hz, 1H), 4.62 (dd, J=11.6, 2.3 Hz, 1H), 4.45 (dt, J=11.6, 5.6 Hz, 1H), 4.17-4.02 (m, 1H), 4.02-3.89 (m, 1H), 3.81 (s, 3H), 2.74-2.50 (m, 2H), 2.49-1.96 (m, 9H), 1.73-1.59 (m, 2H), 1.28 (dd, J=9.6, 4.4 Hz, 2H), 1.21 (d, J=6.3 Hz, 6H), 1.02 (t, J=7.4 Hz, 3H), 0.88 (s, 9H), 0.05 (dd, J=6.0, 3.3 Hz, 6H).

m/z (API-ES, Pos): 680 ([M+NH$_4$]$^+$, 100), 664 (M$^+$, 10)

Step 2: Synthesis of Compound (8)

(Isopropyl7-((1R,2R,3R)-3-(tert-butyldimethylsilyloxy)-2-(4,4-difluoro-3-hydroxyoctyl)-5-oxocyclopentyl)heptanoate)

Example 14

The former prepared compound (7) (57 g, 91% HPLC purity, 0.90 mol), 10% of Pd/C (5.7 g, 53% of H$_2$O) and EtOAc (570 mL) was heated to 60° C. at 0.4 MPa under H$_2$, the reaction was stirred until compound (7) consumed. Then the reaction mixture was filtered through a plug of celite and the filter cake was washed once with EtOAc (285 mL), the filtrate was then concentrated at <55° C. under reduced pressure to give 54 g of compound (8). The residue was purified by column chromatography (EtOAc:n-heptane=1:10) to isolate 47 g compound (8) in 96% crude yield.

Example 15

The former prepared compound (7i) (2.3 g, 89% HPLC purity, 3.5 mmol), 10% of Pd/C (0.23 g, 40% of H$_2$O) and EtOAc (23 mL) was heated to 60° C. at 0.4 MPa under H$_2$, the reaction was stirred until compound (7i) consumed. The reaction mixture was then filtered through a plug of celite and the filter cake was washed once with EtOAc (12 mL), the filtrate was then concentrated at <55° C. under reduced pressure to give 2.0 g of compound (8).

$^1$H NMR (300 MHz, CDCl$_3$): δ 5.07-4.91 (m, 1H), 4.14-4.00 (m, 1H), 3.78-3.58 (m, 1H), 2.65-2.54 (m, 1H), 2.33 (dd, J=6.3, 30.2 Hz, 1H), 2.25 (t, J=7.5 Hz, 3H), 2.17 (dd, J=6.7, 5.3 Hz, 1H), 2.02-1.71 (m, 7H), 1.67-1.25 (m, 14H), 1.22 (d, J=6.3, 6H), 0.93 (t, J=7.2 Hz, 3H), 0.89 (d, J=1.5 Hz, 9H), 0.07 (dd, J=9.3, 2.6 Hz, 6H)

m/z (API-ES, Pos): 549 (M+H$^+$, 100)

Example 16

Step 3: Synthesis of Compound (9)

(Isopropyl7-((1R,2R,3R)-3-(tert-butyldimethylsilyloxy)-2-(4,4-difluoro-3-oxooctyl)-5-oxocyclopentyl)heptanoate)

A solution of oxalyl chloride (1.27 g, 10.0 mmol) in DCM (20 mL) was cooled to −60~−70° C., DMSO (1.56 g, 20.0 mmol) in DCM (5 mL) was added dropwise and the solution was stirred for 30 min. A solution of compound (8) (5.0 g, 9.1 mmol) in DCM (10 mL) was added dropwise and the mixture was stirred for 1 h at −60~−70° C. Et$_3$N (3.04 g, 30.0 mol) was added dropwise into the mixture and the reaction stirred at this temperature until the reaction completed. The mixture warmed to 0° C., water (50 mL) was added to the solution and the mixture was stirred for 5 min. and then separated. The aqueous layer was extracted with DCM (50 mL). The combined organic layer was washed once with sat. NH$_4$Cl (50 mL), once with water (50 mL) and then concentrated at <50° C. under reduced pressure to give 4.57 g compound (9) with 87% HPLC purity in 91% HPLC yield.

$^1$H NMR (300 MHz, CDCl$_3$): δ 5.09-4.91 (m, 1H), 4.03 (q, J=6.7, 1H), 3.00-2.73 (m, 2H), 2.60 (ddd, J=18.1, 6.6, 1.1 Hz, 1H), 2.25 (t, J=7.5, 2H), 2.20 (d, J=7.2 Hz, 1H), 2.14 (d, J=7.2 Hz, 1H), 2.10-1.25 (m, 21H), 1.22 (d, J=6.3 Hz, 6H), 0.92 (t, J=6.9 Hz, 3H), 0.89 (s, 9H), 0.07 (d, J=8.6, 6H)

m/z (EI): 547 (M+H$^+$, 100), 569 (M+Na$^+$, 45)

Example 17

Step 4a: Synthesis of Compound (10)

(7-((1R,2R,3R)-3-(tert-butyldimethylsilyloxy)-2-(4,4-difluoro-3-oxooctyl)-5-oxocyclo pentyl)heptanoic acid)

To a solution of compound (9) (5.0 g, 9.14 mmol) in acetone (15 mL) and pH 7.0 buffer (0.5% NaH$_2$PO$_4$ and adjust pH to 7.0 with 1 N NaOH; 35 mL) was added Lipase PS SD (0.5 g) stirred at 50° C. until compound (9) mostly consumed, the reaction filtrated through a plug of silica gel and wash with MTBE (100 mL), the filtrate washed twice with water (50 mL×2), then concentrate at <40° C. under reduced pressure to give 4.78 g crude compound (10).

$^1$H NMR (300 MHz, CDCl$_3$): δ: 4.03 (q, J=6.7 Hz, 1H), 3.00-2.72 (m, 2H), 2.66-2.55 (dd, J=12.3, 7.5 Hz, 1H), 2.34 (t, J=7.5, 2H), 2.17 (dd, J=18.1, 7.3 Hz, 1H), 2.08-1.17 (m, 22H), 0.92 (t, J=6.9 Hz, 3H), 0.89 (s, 9H), 0.07 (d, J=8.6, 6H)

m/z (ES-API, Neg): 503 ([M−H]$^-$, 35), 371 (100)

Example 18

Step 4b: Synthesis of iPr-Lubiprostone isopropyl7-((2R,4aR,5R,7aR)-2-(1,1-difluoropentyl)-2-hydroxy-6-oxo-octahydrocyclopenta[b]pyran-5-yl)heptanoate To a solution of compound (9) (1.0 g, 1.8 mmol) in MeCN (10 mL), TFA (1.0 g, 8.8 mmol) was added and the mixture was stirred at 15~30° C. for 16 h, TLC analysis showed compound (9) was less than 20%. Water (10 mL) and MTBE (10 mL) were then added and stirred for 5 min. and then separated. The aqueous layer was extracted once with MTBE (10 mL). The combined organic layer was washed twice with water (10 mL×2), once with sat. aq. NaHCO$_3$ (10 mL) and then concentrated at <50° C. under reduced pressure to give 0.85 g crude iPr-Lubiprostone.

Example 19

Step 5a: Synthesis of Lubiprostone Via Compound (10)

(7-((2R,4aR,5R,7aR)-2-(1,1-difluoropentyl)-2-hydroxy-6-oxo-octahydrocyclopenta-[b]pyran-5-yl) heptanoic acid)

To a solution of compound (10) (3.6 g, 7.14 mmol) in MeCN (54 mL), H$_2$SO$_4$ (2 mol/L, 3.57 mL, 7.14 mmol) was added and the mixture was stirred at 15° C.±5° C. until compound (10) consumed. Water (54 mL) was added and extracted twice with MTBE (36 mL×2). The combined organic layer was washed once with sat. aq. NaHCO₃ (36 mL), once with water (36 mL) and dried with anhydrous MgSO₄ and then concentrated at <40° C. under reduced pressure to give 2.58 g crude product with 65% HPLC purity, it was purified by column chromatography to provide 1.3 g Lubiprostone with 80% HPLC purity. Lubiprostone (0.5 g, 80% HPLC purity) was dissolved in MTBE (0.5 mL) at 20~30° C. and n-heptane (2 mL) was then cooled to 0~10° C. with vigorously stirring for 2 h. The solid lubiprostone was filtrated and washed with n-heptane (2 mL), dried at 40° C. under vacuum to give 0.32 g solid lubiprostone.

$^1$H NMR (300 MHz, CDCl₃): δ 4.19 (ddd, J=11.4, 10.0, 7.2 Hz, 1H), 2.58 (dd, J=17.6, 7.2 Hz, 1H), 2.35 (t, J=7.4 Hz, 2H), 2.26 (dd, J=17.7, 11.6 Hz, 1H), 2.10-1.75 (m, 7H), 1.72-1.45 (m, 7H), 1.45-1.22 (m, 8H), 0.94 (t, J=7.3 Hz, 3H)

m/z (ES-API, Neg): 389 ([M−H]⁻, 100)

Example 20

Step 5b: Synthesis of Lubiprostone Via the Isopropyl Ester of Lubiprostone

To a solution of the isopropyl ester of lubiprostone (0.3 g), Lipase PS SD (0.3 g) in acetone (1.5 mL) and pH 8.0 Buffer (2 mL) was stirred at 50~60° C. for 22 h. The reaction solution was concentrated at <50° C. under reduced pressure to give 0.4 g crude product, water (6 mL) and MTBE (6 mL) was added into the residual and stirred for 5 mins, separate and the aqueous layer extracted with MTBE (6 mL). The combined organic layer was washed once with water (6 mL) and once with brine (6 mL) and then concentrated at <50° C. under reduced pressure to give 0.3 g crude product.

Example 21

Step 6: Synthesis of Lubiprostone Salt

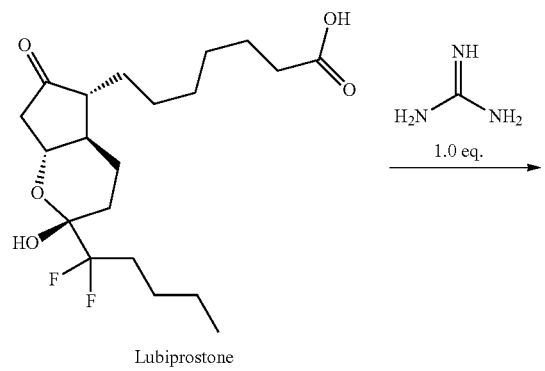

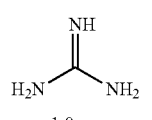

Lubiprostone

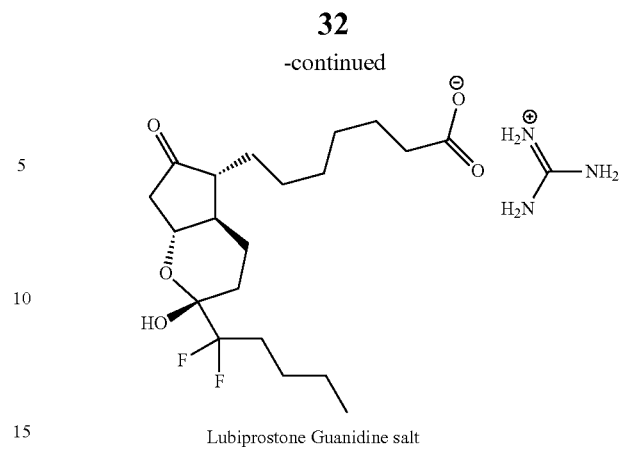

Lubiprostone Guanidine salt

To a solution of guanidine hydrochloride (10 g, 0.105 mol) in MeOH (100 mL) was added a solution of MeONa (4.0 g, 0.105 mol) in MeOH (50 mL) at about 25. The solution was stirred at this temperature for 1 h and a white solid precipitated. The resulting slurry was filtered to remove the precipitated NaCl providing a solution of guanidine in MeOH. To a solution of lubiprostone (0.2 g, 0.513 mmol) in MeOH (2 mL) was added the solution of guanidine in MeOH (0.73 mL, 0.511 mmol) at about 25° C. The mixture was stirred at this temperature for 1 h and then the solvent was evaporated. MTBE (2 mL) was added to the residue at <30° C. and was evaporated under vacuum. This was repeated two more times and then THF (2 mL) was added causing a white solid to form. After stirring at about 25° C. the solid was isolated by filtration to give the guanidine salt of lubiprostone as a white solid. $^1$H NMR analysis of the white solid showed that the methylene signal alpha to the carboxylate group had shifted as compared to free lubiprostone.

$^1$H NMR (300 MHz, CD₃OD): δ=4.22-4.10 (m, 1H), 2.48 (dd, J=17.4, 7.2 Hz, 1H), 2.19 (dd, J=17.4, 11.7 Hz, 1H), 2.16 (t, J=7.5 Hz, 2H), 2.10-1.26 (m, 22H), 0.93 (t, J=7.2 Hz, 3H).

We claim:

1. A process for the synthesis of lubiprostone comprising:
a) coupling of cyclopentenone of formula I:

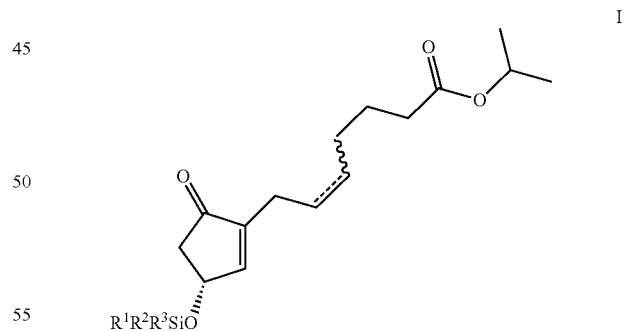

with an organocopper compound of formula III:

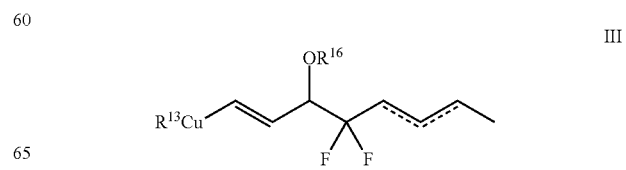

to provide a compound of formula IV:

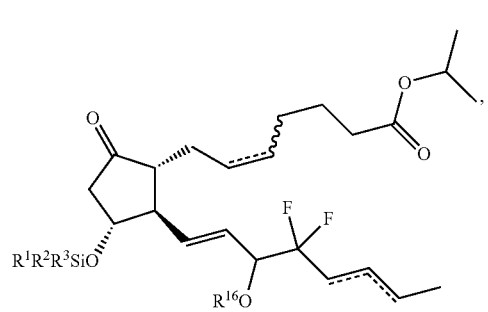

IV b) reacting the compound of formula IV with hydrogen in the presence of a catalyst to provide a compound of formula V:

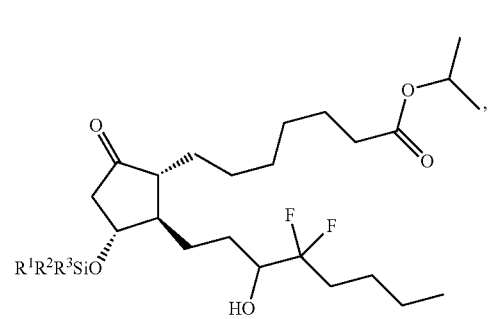

V c) oxidising the compound of formula V to provide a compound of formula VI:

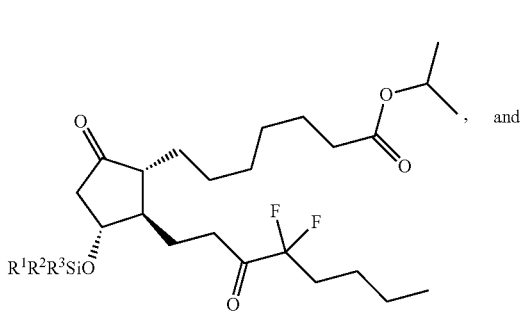

VI

, and d) converting the compound of formula VI to lubiprostone via 1) hydrolysis followed by desilylation or 2) desilylation followed by hydrolysis,
wherein $R^1$, $R^2$, $R^3$ and Si together form a silyl protecting group,
$R^{13}$ is nothing, Li(CN), $Li_2$(CN)Me, $Li_2(CN)_2$-thienyl, Li(CH=CHCH($OR^{17}$)$CF_2CH_nCH_mCH_oCH_3$), or $Li_2$(CN)(CH=CHCH($OR^{17}$)$CF_2CH_nCH_mCH_oCH_3$),
each of n,m and o is 1 or 2 such that either C17 through to C19 is fully saturated or C17 through to C19 contains one single and one double or triple bond,
$R^{16}$ is a substituted or unsubstituted benzyl protecting group, and
$R^{17}$ is a substituted or unsubstituted benzyl protecting group.

2. The process of claim 1, wherein step d) comprises the hydrolysis of the isopropyl ester by aid of an enzyme.

3. The process of claim 1, wherein step d) comprises a step of converting compound of formula VI to a compound of formula VII:

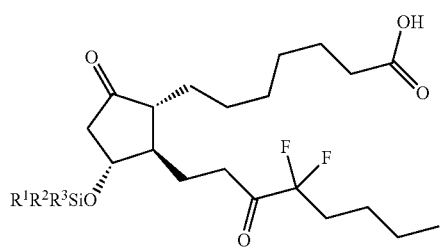

VII

4. The process of claim 1 comprising the following steps for the synthesis of the compound of formula III:

a) reacting a compound of formula VIII:

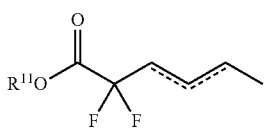

VIII with a silyl protected metal acetylene compound of formula XI:

XI wherein M is a metal ion, to provide a compound of formula IX:

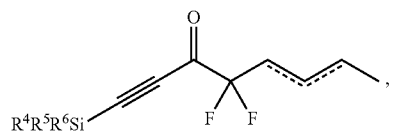

IX b) treating the compound of formula IX with a reducing agent and a desilylating agent to provide a compound of formula X:

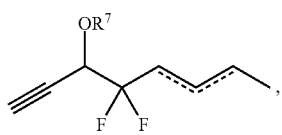

X c) converting the compound of formula X to a compound of formula II:

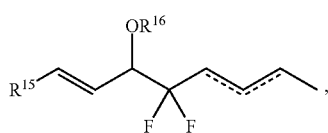

and d) converting the compound of formula II to the compound of formula III, wherein:

R$^4$, R$^5$, and R$^6$ are independently selected from alkyl and aryl;

R$^7$ is hydrogen;

R$^8$, R$^9$, R$^{10}$ are independently selected from alkyl and aryl;

R$^{11}$ is selected from alkyl, benzyl and aryl;

R$^{13}$ is nothing, Li(CN), Li$_2$(CN)Me, Li$_2$(CN)2-thienyl, Li(CH=CHCH(OR$^{17}$)CF$_2$CH$_n$CH$_m$CH$_o$CH$_3$) (each of n,m and o is 1 or 2 such that either C17 through to C19 is fully saturated or C17 through to C19 contains one single and one double or triple bond) or Li$_2$(CN)(CH=CHCH(OR$^{17}$)CF$_2$CH$_n$CH$_m$CH$_o$CH$_3$) (each of n, m and o is 1 or 2 such that either C17 through to C19 is fully saturated or C17 through to C19 contains one single and one double or triple bond);

R$^{16}$ is a substituted or unsubstituted benzyl protecting group;

R$^{17}$ is a substituted or unsubstituted benzyl protecting group; and

R$^{15}$ is SnR$^8$R$^9$R$^{10}$, Br, I or ZrCp$_2$Me.

5. The process of claim 4 wherein M of the compound of formula XI is Li.

6. The process of claim 4 wherein the reaction of compound of formula VIII with a silyl protected metal acetylene compound of formula XI is conducted in the presence of a Lewis acid compound.

7. The process of claim 6 wherein the Lewis acid compound is BF$_3$.

8. The process of claim 4 wherein the reducing agent in step b) is a hydride reducing agent.

9. The process of claim 8 wherein the hydride reducing agent is a metal hydride,
wherein the metal is selected from the group consisting of aluminium, boron, and ruthenium.

10. The process of claim 4 wherein the desilylating agent in step b) is an alkoxide or fluoride reagent.

11. The process of claim 10 wherein the alkoxide reagent is NaOMe.

12. The process of claim 4 wherein step b) is conducted in one reaction vessel without isolation of an intermediate.

13. The process of claim 4 wherein:
the compound of formula II is a compound of formula IIa; and
step c) of converting the compound of formula X to the compound of formula II comprises first attaching SnR$^8$R$^9$R$^{10}$ by reaction of X with a trisubstituted tin hydride in the presence of an initiation agent to produce a compound of formula II', and converting R$^7$ from H to R$^{16}$ by reaction of the compound of formula II' with a base and a benzylation agent to produce the compound of formula IIa:

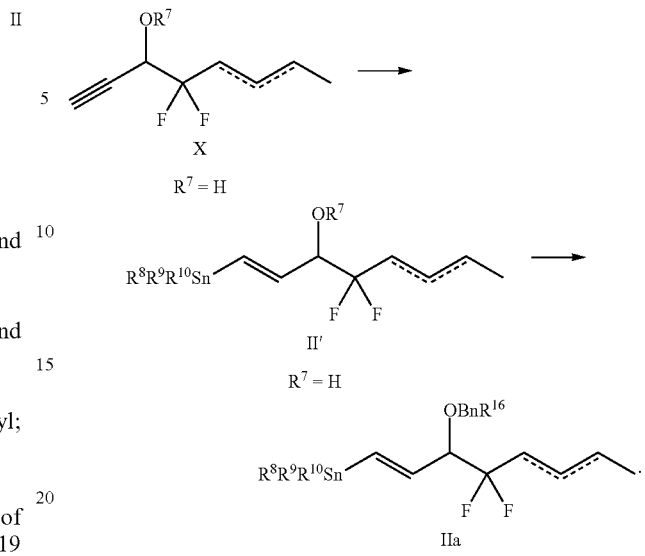

14. The process of claim 4 wherein:
the compound of formula II is a compound of formula IIa; and
step c) of converting the compound of formula X to the compound of formula II comprises first converting R$^7$ from H to R$^{16}$ by reaction of the compound of formula X with a base and a benzylation agent to produce a compound of formula X' and then installing SnR$^8$R$^9$R$^{10}$ by reaction of the compound of formula X' with a trisubstituted tin hydride in the presence of a an initiation agent to produce the compound of formula IIa:

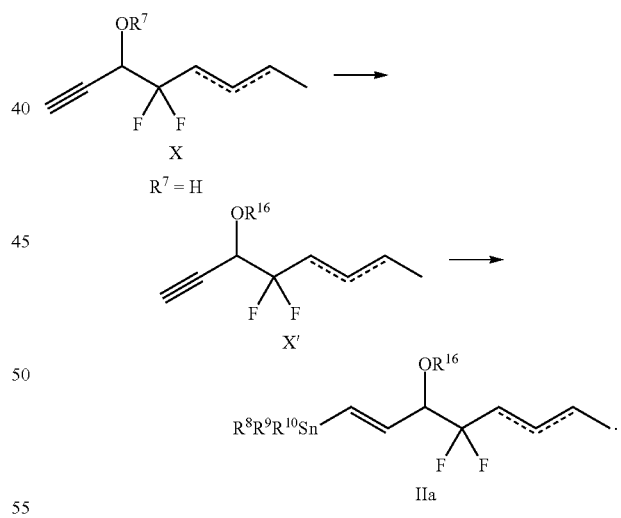

15. The process of claim 4 wherein:
the compound of formula II is a compound of formula IIb; and
step c) of converting the compound of formula X to the compound of formula II comprises first converting R$^7$ from H to R$^{16}$ by reaction of compound of formula X with a base and a benzylation agent to produce a compound of formula X', and then installing ZrCp$_2$Me by reaction of the compound of formula X' with Cp$_2$Zr(H)Cl followed by MeLi to produce the compound of formula IIb:

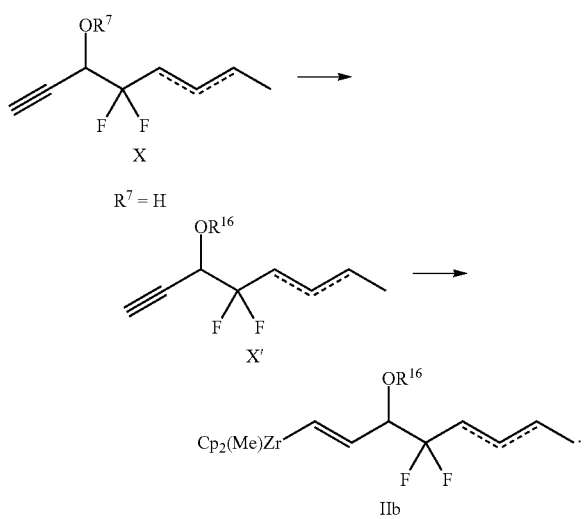

16. The process of claim 4 wherein:
the compound of formula II is a compound of formula IIc; and
step c) of converting the compound of formula X to the compound of formula II comprises first converting $R^7$ from H to $R^{16}$ by reaction of the compound of formula X with a base and a benzylation agent to produce a compound of X' and then installing I by reaction of the compound of X' with $Cp_2ZrCl_2$, t-BuMgCl followed by $I_2$ to produce the compound of formula IIc:

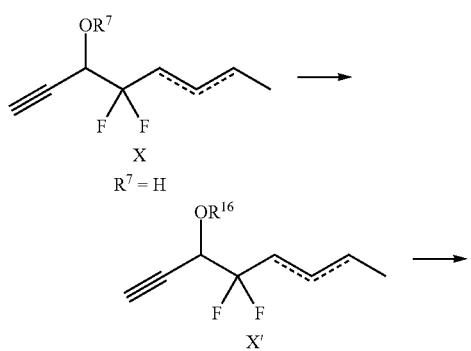

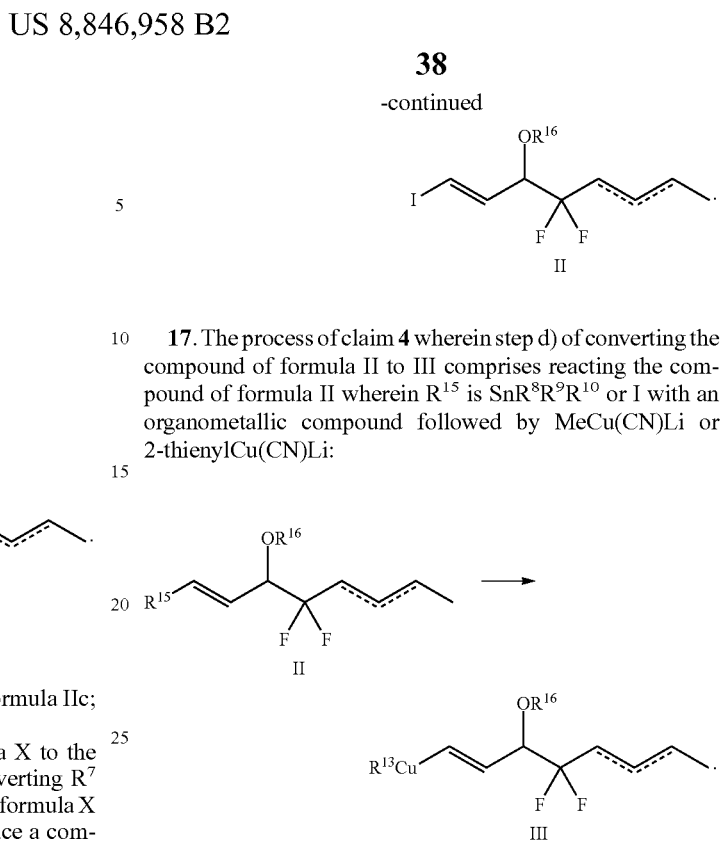

17. The process of claim 4 wherein step d) of converting the compound of formula II to III comprises reacting the compound of formula II wherein $R^{15}$ is $SnR^8R^9R^{10}$ or I with an organometallic compound followed by MeCu(CN)Li or 2-thienylCu(CN)Li:

18. The process of claim 17 wherein the organometallic compound is t-BuLi, s-BuLi or n-BuLi.

19. A process for purifying lubiprostone, comprising synthesizing lubiprostone according to the process of claim 1 and forming a salt of lubiprostone.

20. The process of claim 19, wherein the salt is the guanidine salt.

21. The process of claim 1 wherein the silyl protecting group is tert-butyldimethylsilyl.

22. The process of claim 1 wherein $R^{16}$ is benzyl, methoxy benzyl, or dimethoxy benzyl.

* * * * *